(12) United States Patent
Brito da Silva Correia

(10) Patent No.: US 8,247,581 B2
(45) Date of Patent: Aug. 21, 2012

(54) PROCESS FOR CONVERTING CELLULOSE IN A LIQUID BIOFUEL USING N-METHYL IMIDAZOLIUM CHLORIDE

(75) Inventor: Pedro Manuel Brito da Silva Correia, Estoril (PT)

(73) Assignee: Pedro B Correia, Estoril (PT)

( * ) Notice: Subject to any disclaimer, the term of this patent is extended or adjusted under 35 U.S.C. 154(b) by 185 days.

(21) Appl. No.: 12/476,402

(22) Filed: Jun. 2, 2009

(65) Prior Publication Data

US 2010/0305340 A1 Dec. 2, 2010

(51) Int. Cl.
*C07D 315/00* (2006.01)

(52) U.S. Cl. ....................... 549/417; 549/356

(58) Field of Classification Search .................. 549/417, 549/356
See application file for complete search history.

(56) References Cited

U.S. PATENT DOCUMENTS

2008/0190013 A1* 8/2008 Argyropoulos ................. 44/307
2009/0011473 A1* 1/2009 Varanasi et al. ................. 435/99

FOREIGN PATENT DOCUMENTS

WO   WO 2008/053284   *   5/2008

* cited by examiner

*Primary Examiner* — Andrew D Kosar
*Assistant Examiner* — Valerie Rodriguez-Garcia

(57) ABSTRACT

Process for converting cellulose and hemicellulose in hydroxymethylpyranone and isomers, using as a solvent and catalyst a mixture of N alkyl imidazolium chloride and hydrochloric acid 37%, where hydroxymethylpyranone is extracted with butanol and hydrogenated to methylpyran and isomers.

8 Claims, 2 Drawing Sheets

Figure 1:
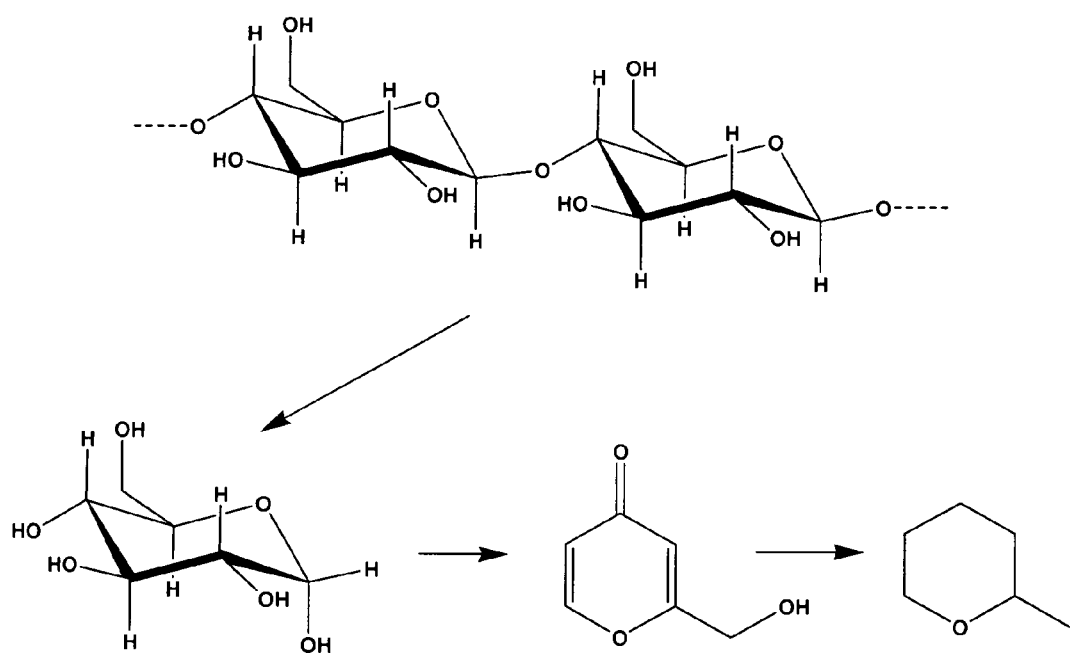
Figure 2:
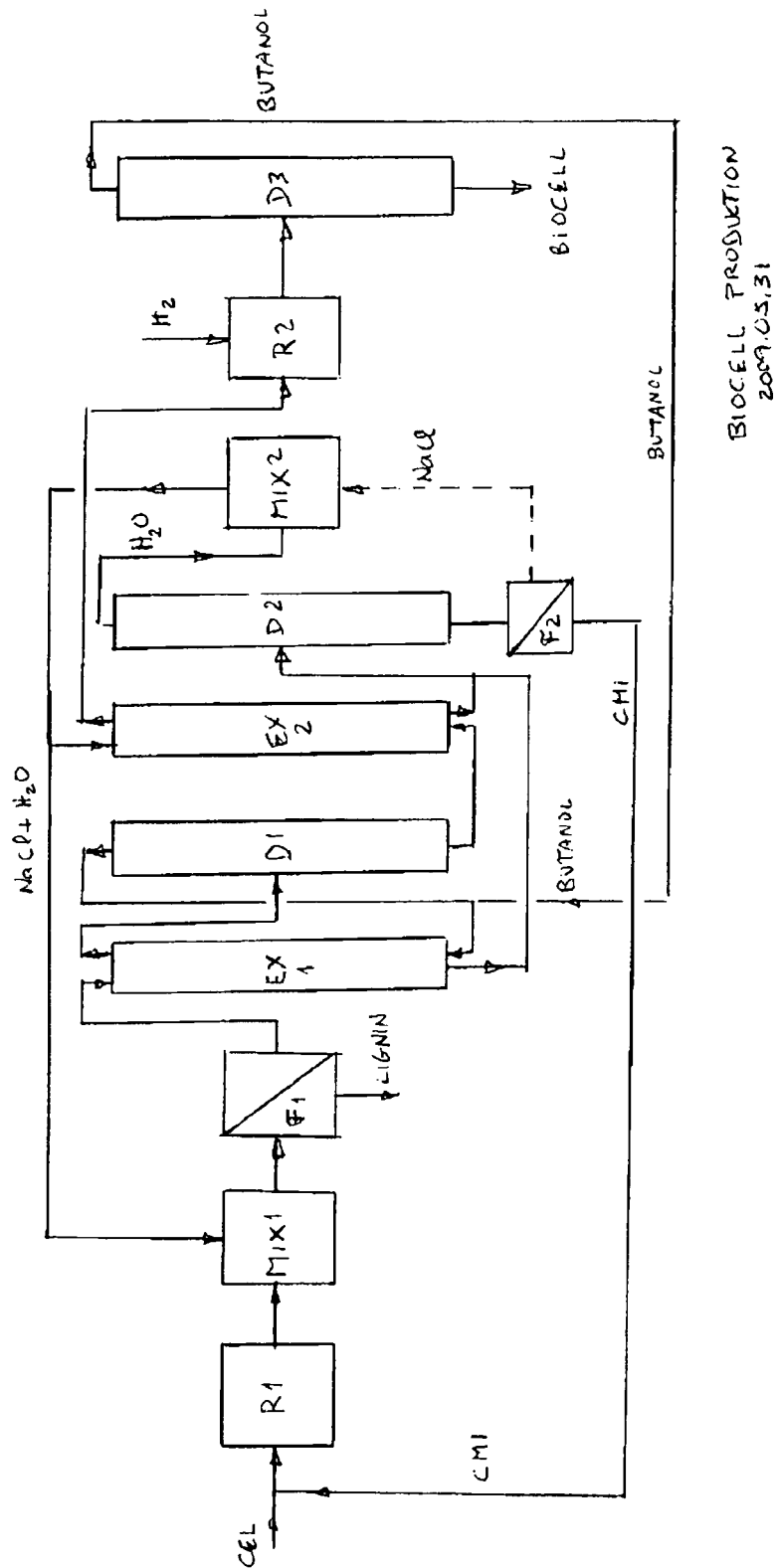

PROCESS FOR CONVERTING CELLULOSE IN A LIQUID BIOFUEL USING N-METHYL IMIDAZOLIUM CHLORIDE

FIELD OF INVENTION

Liquid biofuels from cellulose, ionic liquids, renewable energy, solvent extraction from ionic liquids

BACKGROUND OF THE INVENTION

The world production of cellulose on land is 40 billion ton per year and the stock of cellulose is 700 billion ton.

The world consumption of fossil fuels is 8 billion ton per year.

The food production in the world is 3 billion ton per year.

From these 3 numbers we conclude that to take out from food, materials to produce bio ethanol or vegetable oils for biodiesel would not solve the problem of substituting fossil fuels, and would cause hunger.

On the other side, there are large surfaces of arable land, which are not cultivated or which produce plants not suitable for food. In these surfaces, the production of cellulose from trees or bush is possible. On the other side, cellulose containing biomass is a side product of many food crops.

One of the crops which produce large quantities of cellulose is sugar cane, which has an yield of 80 ton per hectar, In one ton of sugar cane there are about 80 kg of sugar, which may be converted to 50 kg of bioethanol. Besides sugar there are 250 kg of cellulose and hemicellulose, which is a much bigger quantity than sugar, which is not converted to liquid fuels. There are also about 80 kg lignin, which may become a useful energy source in the conversion of cellulose in liquid biofuels.

Cellulose, hemicellulose and starch have been studied in the past as possible sources of raw materials for liquid fuels and chemicals.

Wood itself is since thousands of years an energy source. Biomass is used today to produce electricity, but electricity represents only 10% of the consumption of fossil fuels. It is therefore important to find a process to convert cellulose in liquid fuels, suitable for energy supply to transportation and industry, which represent 90% of the consumption of fossil fuels.

The substitution of fossil fuels is also important because of the carbon dioxide which they produce by burning. Although cellulose also produces carbon dioxide by burning, the same quantity of carbon dioxide was taken out of the atmosphere by photosynthesis to produce cellulose.

Although the carbon dioxide content on earth was up to 6000 ppm 100 million years ago, it decreased to 250 ppm in the nineteen century and increased again up to 380 ppm. This sharp increase in the last century is caused by burning fossil fuels and causes dramatic climate changes due to the greenhouse effect.

As a consequence, to convert cellulose into a liquid fuel is since decades a challenge for scientists, because the existing cars and trucks could drive with such a liquid biofuel without major changes in the motor.

The exhausting oil reserves and the political dependence on unstable countries producing oil is also a major problem today.

Producing electricity from nuclear or from renewable sources like wind, waves, rivers or photovoltaic, is used today, but represents only 20-30% of electricity production. The rest is produced from fossil fuels.

The substitution of liquid fuels by electricity for transports creates a major problem of storage and transportation of electricity, which is technically possible, but far more expensive than the cellulose biofuels (Biocell).

Because cellulose is renewable, abundant and not producing carbon dioxide by burning if photosynthesis is considered, there has been recent scientific work on following subjects (Bibliography 1 to 13):

dissolution of cellulose in ionic liquids instead of traditional processes using water and organic solvents
hydrolysis of cellulose in ionic liquids
dehydration of fructose in ionic liquids to hydroxylmethyl furfural
hydrogenation in organic solvents of hydroxymethyl furfural to isomers of dimethyl tetrahydrofuran
isomerisation of glucose to fructose

DETAILED DESCRIPTION OF THE INVENTION

From our previous work (PCT WO 2008 053284 and PCT IB 2008 03313) we found that the hydrolysis of cellulose to glucose in N-methyl imidazolium chloride (MIC) was always followed by dehydration of glucose and the production of oligomers of glucose both by incomplete hydrolysis of cellulose and by intermolecular dehydration of glucose.

We further found that the conversion of cellulose to dehydration products of glucose was limited by the reversibility of the mentioned reactions.

After the hydrolysis of cellulose in MIC, always an important quantity of cellulose was not hydrolysed. Only a small concentration of hydroxymethyl pyranone (HMP) was formed in the reversible equilibrium, which we could extract with suitable solvents. However, in industry it would be very costly to make the hydrolysis of cellulose to proceed by removing HMP by solvent extraction, according to the unfavourable partition coefficients available at that time.

In fact, the dehydration of glucose requires that the water concentration is small, while to make the extraction with ether or similar solvents, the amount of water in the MIC solution has to be higher, in order to achieve a good partition of HMP between the two phases. A reaction with simultaneous extraction is therefore not interesting.

In the dehydration of glucose up to 3 molecules of water can be lost by internal dehydration. The products so obtained are isomers of hydroxymethyl pyranone. A further dehydration leads to intermolecular loss of water with formation of oligomers and finally carbonisation to graphite.

Previous works (13) refer that the dehydration of glucose in dimethyl formamide gives hydroxymethyl furfural (five atom ring), which is an isomer of HMP (6 atom ring).

In fact, glucose contains in the cyclic form a pyran (6 atom ring) and not a furan (5 atom ring) like fructose. It is not easy to isomerise glucose to fructose by chemical means. Only enzymatic means are really efficient but too slow. On the other side, why to make glucose isomerise from pyranose to furanose if the end result for biofuel is the same?

The hydrogenation of HMP in MIC using current catalysts for hydrogenation like copper chromite, Palladium or Platin on activated carbon or on alumina was not possible because of deactivation of the catalyst by chloride ions.

HMP itself cannot be used as a liquid biofuel, because it is solid at room temperature and unstable. In the literature there are many descriptions of hydrogenations in ionic liquids containing N methyl imidazolium cations with hydrogenosulphate, hexafluorphosphorous and tetrafluorboron anions. The fluorinated anions are unstable in contact with the water, as contained in our reaction mixture.

Therefore we made an experiment with the ionic liquid N methyl imidazolium hydrogenosulphate and found that the equilibrium of the reversible reaction consisting in the dehydration of glucose to HMP and the hydration of HMP to glucose was displaced when HMP was hydrogenated.

The separation of the hydrogenation products of HMP was straightforward both by distillation and by solvent extraction. The distillation is the simplest way, considering that methylpyran has a boiling point around 80° C. while this ionic liquid has a boiling point above 200° C., with decomposition. In the final reaction mixture after hydrogenation, no cellulose precipitated after dilution of 1 g of this mixture in 50 g of water. A clear colourless liquid was obtained.

This process was disclosed by us in U.S. patent application Ser. No. 12/356,643.

We found later a better process with an improved yield, considering the recycling of the reaction solvents including the ionic liquid.

This process is represented in the block diagram. We use as a solvent N alkyl imidazolium chloride containing a small excess of hydrochloric acid 37%, which is necessary to supply water for starting the hydrolysis of cellulose. The pH of MIC is 3 and that is not low enough to catalyse the reactions. The pH was measured after taking 1 g of the MIC solution and diluting in 10 g of water. To allow the hydrolysis the pH must be pH=0.9-1.1.

After the reaction the mixture is filtered to eliminate lignin if the cellulose source is wood.

After filtration, a 10% water solution of sodium chloride is added, in order to make possible the extraction with butanol.

Butanol is miscible with MIC. We found that it is necessary to increase the ionic strength of the MIC solution to make extraction possible.

We tried dozens of other solvents, but found butanol as the best, under the condition that the ionic strength of the MIC solution is increased.

The extract in butanol is concentrated by distillation. The concentrate is extracted with a 10% water solution of sodium chloride, in order to remove the last traces of chloride ions contained in the MIC solution which was passed to the butanol phase.

This extraction is necessary because the catalysts used in the hydrogenation are poisoned by chloride ions.

The butanol extract free from chlorides is then hydrogenated, and later distilled.

FIG. 2

In the block diagram we represent following operations:
in the reactor R1 we make the solution and hydrolysis of cellulose in the mixture N-methyl imidazolium chloride with hydrochloric acid, the dehydration of glucose to hydroxymethyl pyranone and isomers In the tank MIX1 we add the sodium chloride solution for salting out In the filter F1 we separate lignin In the extraction column EXT1 we take the hydroxymethylpyranone and isomers to the butanol phase In the distillation column D1 we separate part of the butanol from the extract of the extraction column EXT1 in order to obtain a butanol concentrate in order to obtain a butanol concentrate containing the hydroxymethyl pyranone In the extraction column EX2 we separate a small quantity of N-methyl imidazolium chloride from the concentrated butanol extract using a water solution of sodium chloride In the destilation column D2 we separate the water from a solution of N-methyl imidazolium chloride containing sodium chloride In the filter F2 we separate N-methyl imidazolium chloride from sodium chloride. Both N-methyl imidazolium chloride and sodium chloride are recycled.

In the tank MIX2 we make the sodium chloride solution with recycled streams of water and sodium chloride In the reactor 2 we make the hydrogenation In the distillation column D3 we separate butanol from methylpyran and isomers (Biocell). Butanol is recycled.

EXAMPLE

| In a stirred glass 250 ml reactor we introduced | |
| --- | --- |
| N methyl imidazolium chloride | 83 g |
| We added slowly | |
| Hydrochloric acid 37% | 100 ml |
| We distilled most of the water and some hydrochloric acid out, until at 0, 1 bar and 90° C. no more water distilled. We obtained a mixture with pH = 1. | |
| We added slowly under stirring | |
| Cellulose | 20 g |
| This mixture was heated at 60° C. during one hour. Then we added: | |
| A 10% solution of sodium chloride in water | 50 g |

After stirring, we extracted 3 times with 100 g butanol each time.

The butanol extracts were evaporated until a volume of 50 ml was reached.

This concentrate was extracted 3 times, each time with 50 ml of a water solution containing 10% sodium chloride in order to eliminate traces of MIC contained in the butanol solution.

The butanol concentrate almost free from chloride ions was introduced in a Parr reactor, as well as 2 g of a catalyst of palladium over alumina. The reactor was inertised 5 times with nitrogen, and heated during 2 hours at 130° C. with a hydrogen pressure of 30 bar. The pressure was maintained by introducing more hydrogen as long as the pressure was lower than 30 bar.

The reaction mixture was cooled, the catalyst was filtered, and the liquid was distilled.

A sample of the final product was injected in a GCMS and submitted to NMR.

An yield of 95% was found, considering that according to stoichiometry 100 g cellulose give 56 g of methylpyran.

Recycling the MIC allowed yields of 85-90% in the following batches.

BIBLIOGRAPHY

1. Jaroslaw Lewkowski, Synthesis, Chemistry and Applications of 5-Hydroxymethyl-furfural and its derivatives, Arkivoc, 2001, 17-54
2. Claude Moreau, Annie Finiels, Laurent Vanoye, Dehydration of fructose and sucrose into 5-hydroxymethylfurfural in the presence of 1-H-3-methyl imidazolium chloride acting both as solvent and catalyst, journal of Molecular Catalysis A, 2006, 165-169

3. Fred Shafizedh, Saccharification of lignocellulosic materials, Pure and Appl. Chem., vol 55, No 4, pp 705-720, 1983
4. Khavinet Lourvanij and Gregory Rorrer, Reaction rates for the partial dehydration of glucose to organic acids in solid-acid molecular sieving catalyst powders J. Chem. Tech. Biotechnol., 1997, 69, 35-44
5. Yuri Roman Leshkov, Christopher Barrett, Zehn Y. Liu, James A. Dumesic, Production of dimethylfuran for liquid fuels from biomass derived carbohydrates, Nature, Vol 447, 21 Jun. 2007, 982
6. Acid in ionic liquid: an efficient system for hydrolysis of lignincellulose, Changzhi Li et al. Green Chemistry, 17 Dec. 2007
7. Cataklytic conversion of cellulose into Sugar alcohols Atsushi Fukuoka et al. Angewandte Chemie, 2006, 45, 5161-5163
9. Pyranone by pyrolysis of cellulose, Fred Shafizadeh, Pure & Appliedd Chem, 1983, 55-4, 705-720
9. Dissolution of cellulose with ionic liquids and its application—a minireview, Shengdong Zhu et al, Green Chemistry, 2006, 8, 325-327
10. WO 2008/053284 A1—Liquid biofuels containing dihydroxymethyl furan, Pedro Correia, priority date 9 Mar. 2007.
11. PCT IB 2008 03313, Liquid biofuels containing 2 methyl tetrahydro pyran, Pedro Correia
12. U.S. patent application Ser. No. 12/356,6643—Liquid biofuels from cellulose, Pedro Correia
13. Simple chemical transformation of lignocellulosic biomass into furan for fuel and chemicals, J. Am. Chem. Soc. 2009, 131, (5), 1979-1985, Joseph Binder, Ronald Raines

The invention claimed is:

1. A process for obtaining a liquid biofuel containing methyl pyran, methyl tetrahydro pyran or its stereoisomers, the process comprising:

a) reacting cellulose with a mixture of N-alkyl imidazolium chloride and hydrochloric acid 37% to form isomers of hydroxymethyl pyranone;
b) adding to the reaction mixture of (a) a 10% sodium chloride water solution;
c) extracting the isomers of hydroxymethylpyranone of step b) with an alcohol;
d) concentrating the alcohol extract;
e) extracting the alcohol concentrate with a 10% sodium chloride water solution to remove traces of N-alkyl imidazolium chloride;
f) hydrogenating the alcohol concentrate of step e); and
g) isolating the biofuel from the hydrogenated alcohol concentrate, whereby step a) is performed under reaction conditions which allow the hydrolysis of cellulose while avoiding the pyrolysis of glucose, wherein the pH of step a) is 0.9 to 1.1.

2. The process of claim 1, wherein the alkyl of N-alkyl imidazolium chloride contains 1 to 10 carbon atoms.

3. The process of claim 1, wherein the temperature of the reaction of step a) is 40° C. to 120° C.

4. The process of claim 1, wherein the alcohol used in step c) is n-butanol.

5. The process of claim 1, wherein step d) is performed by distillation.

6. The process of claim 1, wherein the hydrogenating hydrogenation of step f) is performed with hydrogen gas at a pressure of 2 to 100 bar, and at a temperature of 50° C. to 180° C.

7. The process of claim 1, wherein step g) is performed by distillation.

8. The process of claim 1, further comprising recycling the N-alkyl imidazolium chloride.

* * * * *